US006547738B2

(12) United States Patent
Lysyansky

(10) Patent No.: US 6,547,738 B2
(45) Date of Patent: Apr. 15, 2003

(54) METHODS AND APPARATUS FOR USING ULTRASOUND WITH CONTRAST AGENT

(75) Inventor: Peter Lysyansky, Haifa (IL)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/681,589

(22) Filed: May 3, 2001

(65) Prior Publication Data

US 2002/0165455 A1 Nov. 7, 2002

(51) Int. Cl.[7] ............................................. A61B 8/06
(52) U.S. Cl. ........................ 600/458; 600/442; 600/443; 600/437
(58) Field of Search ................................. 600/437–472

(56) References Cited

U.S. PATENT DOCUMENTS

| 5,255,683 | A | * | 10/1993 | Monaghan | 600/458 |
|---|---|---|---|---|---|
| 5,456,257 | A | | 10/1995 | Johnson et al. | 128/662.02 |
| 5,509,413 | A | | 4/1996 | Akama et al. | 128/660.02 |
| 5,560,364 | A | | 10/1996 | Porter | 128/662.02 |
| 5,577,505 | A | | 11/1996 | Brock-Fisher et al. | 128/662.02 |
| 5,601,085 | A | | 2/1997 | Ostensen et al. | 128/662.02 |
| 5,678,553 | A | | 10/1997 | Uhlendorf et al. | 128/662.02 |
| 5,722,403 | A | * | 3/1998 | McGee et al. | 600/373 |
| 5,735,281 | A | | 4/1998 | Rafter et al. | 128/662.02 |
| 5,743,266 | A | | 4/1998 | Levene et al. | 128/662.02 |
| 5,749,364 | A | | 5/1998 | Silwa et al. | 128/662.02 |
| 5,820,561 | A | | 10/1998 | Olstad et al. | 600/453 |
| 5,833,613 | A | | 11/1998 | Averkiou et al. | 600/440 |
| 5,860,931 | A | * | 1/1999 | Chandler | 600/458 |
| 5,935,069 | A | | 8/1999 | Chandler et al. | 600/443 |
| 5,944,666 | A | * | 8/1999 | Hossack et al. | 600/454 |
| 5,947,904 | A | * | 9/1999 | Hossack et al. | 600/458 |
| 5,961,464 | A | | 10/1999 | Poland | 600/458 |
| 5,971,928 | A | | 10/1999 | Dodd et al. | 600/458 |
| 6,004,270 | A | | 12/1999 | Urbano et al. | 600/443 |
| 6,015,384 | A | | 1/2000 | Ramamurthy et al. | 600/440 |
| 6,017,310 | A | | 1/2000 | Johnson et al. | 600/458 |
| 6,068,600 | A | | 5/2000 | Johnson et al. | 600/458 |
| 6,077,225 | A | | 6/2000 | Brock-Fisher | 600/439 |
| 6,080,107 | A | | 6/2000 | Poland | 600/458 |
| 6,086,540 | A | | 7/2000 | Bonneville et al. | 600/458 |
| 6,149,597 | A | | 11/2000 | Kamiyama | 600/458 |

* cited by examiner

Primary Examiner—Francis J. Jaworski
Assistant Examiner—William C Jung
(74) Attorney, Agent, or Firm—McAndrews, Held & Malloy, Ltd.; Peter J. Vogel; Michael A. Dellapenna

(57) ABSTRACT

Methods and apparatus for producing zones with different contrast agent concentrations in a contrast agent infused target. An aspect of the method is subjecting the target to an ultrasound flash capable of producing first and second target zones, the first target zone having a higher concentration of contrast agent than the second target zone. Another aspect of the method is forming an ultrasound image of the target, wherein the first and second target zones in the ultrasound image have different ultrasonic responses. An embodiment of the apparatus of the present invention comprises a front-end controller (FEC) for use in a medical imaging system wherein the FEC controls a transducer to selectively radiate, in a single frame, a first beam position at a first energy and a second beam position at a second energy.

28 Claims, 2 Drawing Sheets

METHODS AND APPARATUS FOR USING ULTRASOUND WITH CONTRAST AGENT

BACKGROUND OF INVENTION

The present invention is directed to methods and apparatus for using ultrasound with contrast agent. More particularly, the present invention is directed to methods and apparatus for using ultrasound to produce regions of a target area in which the concentrations of contrast agent are different.

Contrast agents may be used with diagnostic ultrasound to improve the image quality of a target area. Typically, contrast agents contain small particles, such as microbubbles, with high scattering capability. By injecting contrast agent into the bloodstream of a patient, contrast agent flows into the tissue to be imaged and ultrasound waves directed at the imaged tissue are scattered, thereby increasing the signal-to-noise ratio. The increased signal-to-noise ratio improves the quality of the ultrasound images, whether in the 2D, M, Doppler, or color Doppler modes.

Contrast agents have other benefits besides image enhancement. The temporal dynamics of some contrast agents provide information about blood circulation. The signal intensity, and thus the image brightness, is typically greater for greater contrast agent concentrations. After the initiation of contrast agent injection, the image brightness increases over time up to a saturation level. The rate of that change in image brightness is typically related to the rate of increase in contrast agent concentration.

Blood perfusion or local blood supply may be an important aspect of a patient"s medical condition in a given body region. Blood perfusion has been conventionally estimated using contrast agent by measuring the time required for the image of a given body region to reach a brightness level associated with a pre-selected reference level.

Blood perfusion measurements may be used for specific clinical purposes. For detecting malignancies, the blood supply in malignant tissue is higher than in surrounding body areas. Thus, malignant tissue can be detected because the brightness of the image of malignant tissue increases faster and reaches the saturation level faster than healthy tissue, following injection of contrast agent. For detecting ischemic myocardial heart muscle segments, the pathological region is characterized by a slow rate of increase in image brightness following injection of contrast agent. This is so because myocardial segments suffer from a deficiency in blood supply.

Conventional methods, such as the two examples above, are based on the measurement of the time for the contrast agent concentration to rise. The concentration rise time is a relative parameter, so the diagnostic conclusion may be based on a comparison between defective tissue portions and healthy tissue portions.

In one method of measuring perfusion, the concentration rise time measurement should start from a low contrast agent concentration. One typical method of measuring rise time from a low contrast agent concentration is to start brightness measurements at the beginning of the contrast agent injection. Such a method is not very accurate because excessive time may be needed for contrast agent to be delivered to the target area by main blood flow. Also, the time for contrast agent to be delivered to the target area by main blood flow can vary for different body parts due to blood vessel structure. Delivery time should be taken into account in the calculation of perfusion rates when brightness is measured from the beginning of the contrast agent injection. Consequently, the accuracy of the perfusion rate calculations is decreased significantly when brightness measurements are started at the beginning of the contrast agent injection.

Another way to measure rise time is to use ultrasound to destroy contrast agent bubbles in a "flash." A flash is a relatively powerful ultrasound scan comprising a frame or frames capable of destroying contrast agent. A flash may be characterized by a number of parameters including energy, frequency, or pulse duration. Even an ultrasound flash or burst of moderate amplitude is capable of destroying bubbles because of the low stability of bubbles in many contrast agents.

The starting point of a rise time measurement may be defined by the end of a flash. The flash produces a clean region, which is the target tissue while the target tissue has relatively little or no contrast agent. The clean region has a minimal brightness that corresponds to a suitable starting point for rise time measurement. Continuous contrast agent infusion maintains a high, stable level of contrast agent generally throughout the body except for the clean region just after the flash. After the flash, the contrast agent penetrates the clean region at the rate of the local blood perfusion, increasing the brightness of the clean region until the clean region is no longer clean but rather has reached a saturation point of contrast agent. Changes in the image brightness of the clean region may be monitored by using low power scanning or other methods of imaging to view that region from a period starting immediately after the flash.

The conventional flash method, however, has some deficiencies. Different parts of the target tissue may differ in brightness because of differences in depth. Time-varying acoustical shades might be due to contrast agent concentration variations in more shallow regions. These effects can disturb the estimation of rising time, because different portions of the target tissue reach the saturation level of brightness at different times.

Another deficiency of the conventional flash method results from the influence of image movement. Breathing, heart contractions, and probe movement are examples of types of image movements, and such movements can affect the local brightness in images of the target tissue. Heart movement in particular can be a major problem for cardiac imaging applications. Changes in local brightness thus might not only be attributable to variations in contrast agent concentration but also to complicated shaded-image movement.

The problem of shaded-image movement changing local brightness could be partially solved by ECG-triggered imaging. In ECG-triggered imaging, changes in brightness would be checked at only one time during a heart cycle.

Tissue tracking could be used to follow a tissue segment that is being analyzed, but this type of tissue tracking can be inaccurate, especially in the presence of time-varying contrast agent concentration. One reason for the inaccuracy is that the source of contrast agent for the tissue segment might not be local to the tissue segment, causing the measurements of the rate of change of brightness to reflect distance rather than actual perfusion rate.

Heart muscle health is often assessed by the observation of myocardium dynamics (i.e., contracting/stretching). One example is the Stress Echo procedure. The procedure is based on subjective estimation and depends strongly on a doctor's -experience. The estimation is based on the image quality, which is very poor for some difficult patients. There is a need for an objective numerical criterion for contractility level.

SUMMARY OF INVENTION

In accordance with at least one preferred embodiment, a method is provided for producing zones with different contrast agent concentrations in a target. The method comprises the step of subjecting the target to an ultrasound flash capable of producing first and second target zones, the first target zone having a higher concentration of contrast agent than the second target zone. Another embodiment of the present invention is a method for producing an ultrasound image of a contrast agent infused target. The method comprises the steps of producing first and second target zones, the first target zones having a higher concentration of contrast agent than the second target zones, and forming an ultrasound image of the target, wherein the first and second target zones in the ultrasound image have different ultrasonic responses. The ultrasound flash may have a non-homogeneous energy distribution. The first and second target zones may form a plurality of stripes. Some embodiments of the present invention may be used to estimate blood perfusion rates. Some embodiments of the present invention may be used to estimate contractility of the heart.

Another aspect of the present invention is an ultrasound imaging system that includes a front-end controller (FEC), wherein the FEC controls a transducer to selectively radiate in different beam positions within a single frame at one of a plurality of energies. In the ultrasound system, a plurality of beam positions forming a first transmission region may have a first energy and a plurality of beam positions forming a second transmission region may have a second energy. Another embodiment of the invention is an FEC for use in a medical imaging system wherein the FEC controls a transducer to selectively radiate in different beam positions within a single frame at one of a plurality of energies. A further embodiment is an ultrasound system in which beam positions of a transducer are arranged to produce first and second transmission regions, wherein no beams are in the first transmission regions and at least one beam is in each of the second transmission regions.

BRIEF DESCRIPTION OF DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION

Figure 1:
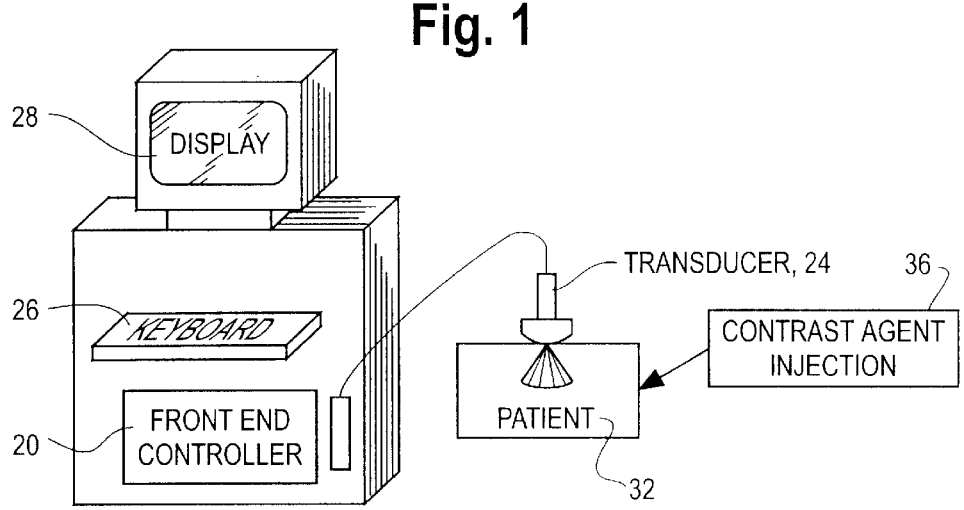
FIG. 1 is a schematic of an embodiment of the present invention.
Figure 2:
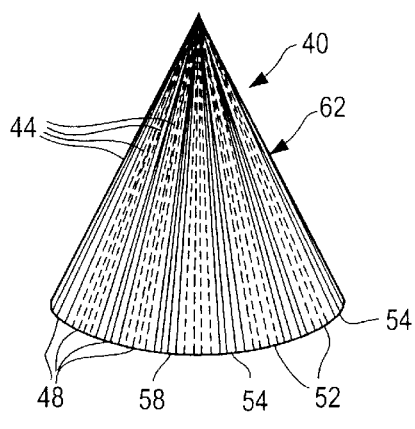
FIG. 2 is a schematic illustration of a flash frame in accordance with one embodiment of the present invention.

An embodiment of the present invention is shown in FIG. 1 and comprises a front end controller (FEC) 20, a transducer 24, a keyboard 26, and a display 28. Also shown in FIG. 1 is a patient 32 that receives contrast agent via contrast agent injection 36. The FEC 20 controls the transducer 24 to produce frames 40 (FIG. 2). Each frame 40 comprises a plurality of ultrasound beams 44 or lines. The number of beams 44 depends on the ultrasound machine and the medical application. A few dozen beams 44 up to a few hundred beams 44 are typical in a frame 40.

Each beam 44 is defined by a set of parameters, which includes direction (transmit angle), focal position, transmit frequency, transmit energy, and pulse length. The parameter sets for different beams 44 in the same frame 40 may be different. The parameter sets for the beams 44 of a frame 40 are collected into a preset table (not shown).

As shown in the embodiment of the present invention depicted in FIG. 2, each frame 40 comprises at least two transmission regions 48. A first transmission region 52 has a relatively low energy and a second transmission region 54 has a relatively high energy.

The transmitted energy of the first and second transmission regions 52, 54 may be determined by a number of methods, not limited to the following examples. Energy may be transmitted in every angle of a frame 40 and an operator selects which beam angles will transmit at relatively high energy and which beam angles will transmit at relatively low energy. One way to control the energy to be transmitted at different angles is to use the FEC 20. The FEC 20 controls the transducer 24 to selectively radiate, within a single frame 40, a first beam position at a first energy and a second beam position at a second energy. FIG. 2 depicts an embodiment of the invention in which energy is transmitted in every angle of the frame 40. Thus, using the preset table, an operator may select both the energy of each transmitted beam 44 and the direction in which the energy of each beam 44 may be transmitted.

Each transmission region 52, 54 can be formed from one to about a few dozen beams 44, preferably 2–10 beams 44, and more preferably 4–6 beams 44. In some embodiments of the present invention, the frame or frames 40 comprise a plurality of the first transmission regions 52 and a plurality of the second transmission regions 54. In embodiments with a plurality of the first transmission regions 52, the number of beams 44 in a first transmission region may be different than the number of beams 44 in other first transmission regions 52. Similarly, the number of beams 44 in a second transmission region may be different than the number of beams 44 in other second transmission regions 54. The number of beams 44 in the first transmission regions 52 may be different than the number of beams 44 in the second transmission regions 54. It should be noted that an operator may select the energy of the first transmission region 52 to be zero in the embodiment shown in FIG. 2.

Figure 3:
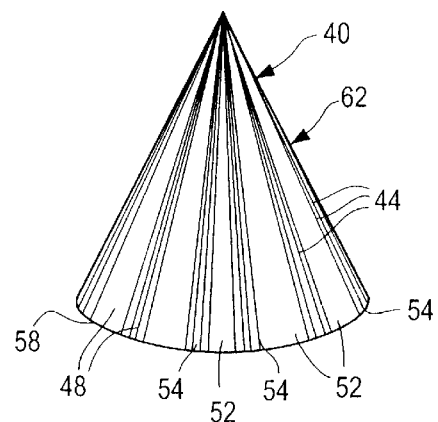
FIG. 3 is a schematic illustration of a flash frame in accordance with another embodiment of the present invention.

An operator may steer the beams 44 by selecting the desired directions in which to transmit ultrasound energy and selecting the directions in which no ultrasound energy will be transmitted. As seen in FIG. 3, beams 44 may be directed at angles in such a way that the first and second transmission regions 52, 54 are formed. The beams 44 are not all arranged in an equal angle step in the embodiment of FIG. 3. By steering the ultrasound beams 44, energy can be propagated in the second transmission regions 54 without propagating energy in the first transmission regions 52.

An aspect of the present invention is the use of an ultrasound machine to subject a contrast agent infused target 58 to a non-homogeneous energy distribution 62 to produce first and second target zones 64, 68 having, respectively, relatively high and low contrast agent concentrations. The general area to be imaged is the target 58. The first and second transmission regions 52, 54 are used to produce the first and second target zones 64, 68 by causing more contrast agent to be destroyed in the second target zone or zones 68 than in the first target zone or zones 64.

Immediately following a flash comprising a non-homogeneous energy distribution 62, the first target zones 64 have a higher concentration of remaining contrast agent than do the second target zones 68. In ultrasound imaging in general, a scanned area with relatively little contrast agent appears darker than a scanned area having more contrast agent. Thus, when imaged, the first target zones 64 are generally brighter than the second target zones 68 immediately after the flash. After the flash has occurred, the ultrasound scanner may be set to a screen mode to observe the pattern of first and second target zones 64, 68. Cine mode memory may be used to record and replay the scans of the first and second target zones 64, 68 following a flash.

Sequences of flash frames 40 comprising non-homogeneous energy distributions 62 and sequences of imaging frames 70 may be performed in succession multiple times.

Figure 5:
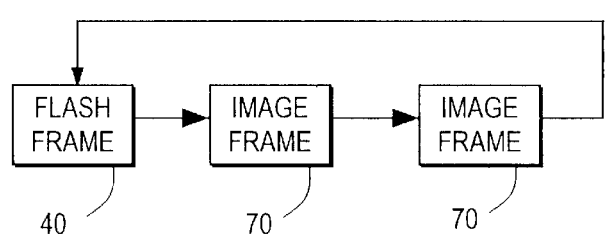
FIG. 5 is a flow chart of steps in accordance with a further aspect of the present invention.

FIG. 5 depicts one possible set of flash frame 40 and imaging frame 70 sequences.

Suitable contrast agents include, but are not limited to, agents comprising microbubbles or microspheres. Such agents are said to undergo destruction when some or all of the microbubbles or microspheres are burst by the ultrasound beams 44.

In order to produce the first and second target zones 64, 68, the flash is capable of destroying more contrast agent in some areas (i.e., the second target zones 68) than in other areas (i.e., the first target zones 64). The flash comprises interleaved first and second transmission regions 52, 54. The second transmission region 54 is a relatively high energy region that destroys more contrast agent than the first or low energy transmission region 52 destroys. The energy of a transmitted ultrasound pulse equals the squared amplitude of the transmitted ultrasound pulse. It is to be understood that the non-homogeneous energy distribution 62 in a flash in accordance with embodiments of the present invention could be characterized by amplitude, power, or intensity, instead of energy.

A number of beam 44 parameters may be varied to create the first and second transmission regions 52, 54. Energy and beam 44 direction are two of those beam 44 parameters, as discussed above. Frequency and pulse length are two other beam 44 parameters that may be varied, individually or collectively to create the first and second transmission regions 52, 54. Although only the parameter energy is discussed in detail below, an operator could vary any combination of pulse length, frequency, direction, or energy, to create the first and second transmission regions 52, 54 for use with various contrast agents. The optimal frequency, energy and pulse length may be selected in order to maximize the contrast agent destruction in the second target zones 68. Specific levels of energy that are suitable for the second transmission regions 54 may depend on the application. For medical purposes, for example, safety concerns may limit the amount of energy employed in the second transmission regions 54.

The frame or frames 40 of the flash may have a duration that is typical for a frame. Although the flash of non-homogeneous energy distribution 62 may comprise a plurality of frames 40, for best results, it may be most effective to have the total duration of the flash be relatively brief. Otherwise, in some applications, the target tissue might move significantly during the flash, causing the first and second target zones 64, 68 to overlap on the target tissue, resulting in less distinct first and second target zones 64, 68.

Following a flash frame 40, an operator may scan using imaging frames 70 to reveal the first and second target zones 64, 68 formed by the flash frame 40. The first target zones 64 appear brighter than the second target zones 68 because the first target zones 64 have a higher concentration of contrast agent than the second target zones 68. FIG. 5 is a block diagram showing a sequence of steps in a connection with the present invention. The number of flash frames 40 performed prior to imaging may be varied depending on the application. Also, the number of imaging frames 70 may be varied, depending on the contrast agent, among other factors. As shown in FIG. 5, flash frames 40 can be performed following imaging frames 70 to repeat the process of flashing and imaging. Imaging frames 70 generally have parameters that are selected to minimize contrast agent destruction while providing quality imaging of the target 58. Suitable energy, pulse length, and frequency, among other parameters, may be selected by an operator to provide quality imaging.

Figure 4:
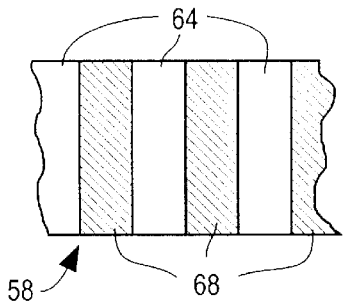
FIG. 4 is a schematic illustration of an embodiment of target zones in accordance with an aspect of the present invention.

In one embodiment of the present invention, the patient 32 (FIG. 1) is given contrast agent that infuses a target area 58 (FIG. 4). The contrast agent may be almost any typical contrast agent that is selectively destroyed by varying ultrasound parameters such as transmitted energy, pulse length, or frequency. As noted earlier, contrast agents comprising microspheres or microbubbles are generally suitable.

Although not limited to continuous infusion of contrast agent, continuous infusion of contrast agent may produce better results than a bolus in some embodiments. Time-related variation in concentration caused by a bolus may potentially confound comparisons of brightness between first and second target zones 64, 68.

Following infusion with contrast agent, the target area 58 of the patient 32 is subjected to an ultrasound flash that comprises the first and second transmission regions 52, 54. The first transmission region 52 destroys relatively little contrast agent compared to the second transmission region 54. The ultrasound energy distribution is thus non-homogeneous.

The flash will have created the first and second target zones 64, 68 having relatively high and relatively low concentrations of contrast agent, respectively. Following the flash, imaging of the target area 58 will reveal relatively bright and relatively dark regions forming a pattern of acoustic markers. The relatively bright regions correspond to the regions with a relatively high concentration of contrast agent, and are the regions associated with the first transmission regions 52. The relatively dark regions correspond to the regions with a relatively low concentration of contrast agent, and are the regions exposed to ultrasound energy from the second transmission regions 54.

One method in accordance with this invention produces first and second target zones 64, 68 having detectably different ultrasound responses. For some medical applications, it is preferred to produce first and second target zones 64, 68 having substantially different ultrasound responses because substantially different ultrasound responses are readily distinguishable and measurable by an operator or an ultrasound machine.

The energy of the beams 44 that are directed toward the second target zones 68 have an energy greater than zero. In some embodiments, the beams 44 that are directed toward the first target zones 64 have zero energy and, consequently, the first target zones 64 would receive no ultrasound energy (or, at most, a little stray energy from the second transmission regions 54) even though some beams 44 are directed toward the first target zones 64. First transmission regions 52 in which the beams 44 have no energy would result in first target zones in which the contrast agent concentration remaining after the flash of non-homogeneous energy distribution 62 is about the same as the contrast agent concentration prior to the flash.

In embodiments in which the ultrasound beams 44 are steered, energy may be propagated in the second transmission regions 54 but not propagated in the first transmission regions 52. Such first transmission regions 52 would result in first target zones 64 in which the contrast agent concentration remaining after the flash of non-homogeneous energy distribution 62 is about the same as the contrast agent concentration prior to the flash.

Figure 6:
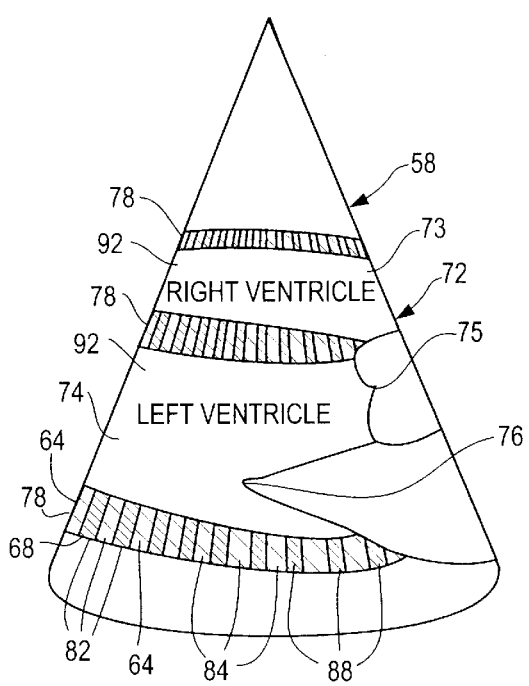
FIG. 6 is a schematic illustration of an ultrasound scan of a heart shown immediately or a few seconds following a flash in accordance with an aspect of the present invention.
Figure 7:
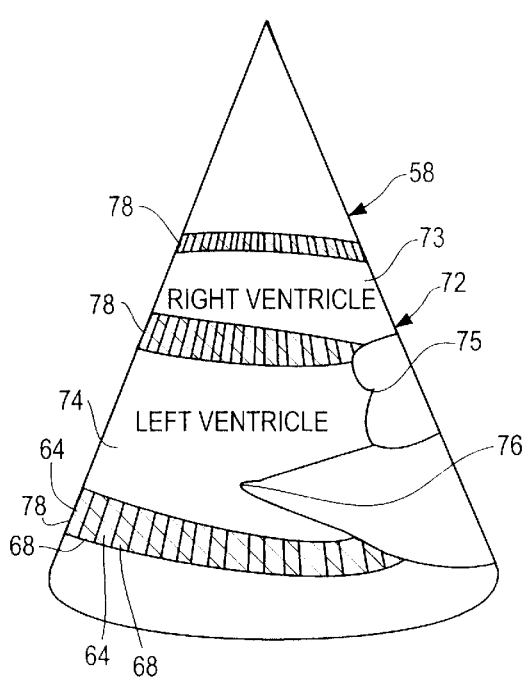
FIG. 7 is a schematic illustration of an ultrasound scan of the heart section shown in FIG. 6 and taken after the scan shown in FIG. 6.

FIGS. 6 and 7 depict a myocardium or heart 72 to illustrate further embodiments of the present invention. In the view shown, a right ventricle 73, a left ventricle 74, an aortic valve 75, and a mitral valve 76 can be seen. Blood perfusion rate into the three tissue areas 78 of the heart 72 shown in FIGS. 6 and 7 can be important for determining blood supply to the heart 72. Some aspects of the present invention facilitate examination of blood perfusion rates in the three tissue areas 78 shown and into other areas (not shown) of the heart during ultrasound scans.

In the embodiment of FIGS. 6 and 7, after the flash of non-homogeneous energy distribution 62, stripes 82 are formed on part of the imaged target area 58. The stripes 82 are one of the forms that the acoustic markers of embodiments of the present invention may comprise. Prior to the flash, the target area 58 was saturated with contrast agent. FIG. 6 depicts an illustration of an ultrasound image of a parasternal long axis cross-section of the heart 72. The first target zones 64 are white stripes 84 and the second target zones 68 are black stripes 88. The embodiment of the present invention that produced the stripes 82 shown in the tissue in FIG. 6 thus produced first and second target zones 64, 68 having substantially different ultrasound responses. Some embodiments of the present invention produce first and second target zones 64, 68 having detectably different ultrasound responses that are not substantially different.

FIG. 6 represents the heart 72 about one or two heartbeats after the flash. There are no stripes 82 in blood 92 in FIG. 6 because stripes 82 in blood 92 within major heart blood volumes would disappear very quickly in the bloodstream after the flash as fresh blood 92 rapidly brings in additional contrast agent. The blood 92, which quickly reaches a saturation concentration of contrast agent after the flash, is shown as white. The three tissue areas 78 shown in FIG. 6 are still striped after a few heartbeats following the flash, allowing analysis of heart 72 as discussed below.

FIG. 7 is a depiction of an ultrasound image of the same section of the heart 72 as shown in FIG. 6, but at least a few seconds (and possibly a few minutes) have passed since the image of FIG. 6 would have been viewed on an ultrasound display. The time between an image such as seen in FIG. 6 and an image as seen in FIG. 7 may vary depending upon the type of contrast agent, the blood flow rate, and other variables.

In FIG. 7, the second target zones 68 have become substantially as bright as the first target zones 64 because blood flow into the heart tissue area 78 has replenished contrast agent in the depicted heart section, bringing the concentration of contrast agent up to nearly the concentration in the first target zones 64. The first target zones 64 in FIG. 6 are substantially the same brightness as the first target zones 64 in FIG. 7 because those target zones were subjected to relatively low (or no) destructive ultrasound waves during the flash that preceded (by a few seconds) the image shown in FIG. 6.

Stripes 82 of at least about 1 mm in width are generally suitable for many applications. Stripe widths of 3–5 mm are readily visible during scanning, which may be desirable for some applications. Stripes 82 of greater than about 10 mm in width may be employed in accordance with some embodiments of the present invention, but such wide stripes 82 have a few drawbacks. First, fewer wide stripes 82 fit into the target area 58 than narrow stripes 82. Thus, few stripes 82 wider than 10 mm will fit into the imaged area.

Second, the tissue in the center of a wide stripe 82 is farther from the tissue in the center of an adjacent wide stripe 82 compared to the distance between the center of a narrow stripe 82 and the center of an adjacent narrow stripe 82. The blood flow phenomena or tissue characteristics in one wide stripe 82 are not as likely to be representative of the blood flow phenomena or tissue characteristics of an adjacent wide stripe 82 as would be the case with a narrow stripe 82 and an adjacent narrow stripe 82. The relatively long distance between the center of a wide stripe 82 and the center of an adjacent wide stripe 82 may increase the likelihood that different tissue depth or other factors would be the actual cause of observed differences in perfusion rate. Thus, relatively narrow stripes 82 may be more suitable for measuring blood perfusion rate and other phenomena.

Five to ten stripes 82 per imaged area are preferred for some embodiments of the present invention, however, fewer stripes or more stripes 82 may be suitable. If the target area is magnified during imaging, it is possible that not all of the stripes 82 produced on the target by the FEC 20 and transducer 24 will be visible during imaging. Thus, an operator may take into account desired magnification levels when determining how many stripes 82 should be produced for a particular application. More stripes may be necessary if high magnification is expected to be employed. The number of stripes 82 desired for a particular application may, in turn, determine the width of the stripes 82 for that application.

In some cases, energy is non-homogeneously distributed along the beam 44, because the beam 44 is conical. Stripes 82 may be formed using beams 44 that are conical. The focal point of the beam 44 has the highest contrast agent destruction capability. In some applications, the focal shape or shape of the beam 44 may be controlled to make the focal point of a narrow beam 44 with higher energy. Such a shaped beam 44 could then destroy much more contrast agent near the focal point than at other points of the same beam 44. Narrow focal points, however, are not possible for some applications, including ultrasound probes for some cardiac applications.

The more contrast agent destroyed by the second transmission regions 54 and the less contrast agent destroyed by the first transmission regions 52, the greater the ultrasound response difference created between neighboring regions of the target area 58. For example, if stripes 82 are formed by the first and second transmission regions 52, 54, then adjacent stripes 82 will have greater ultrasound response differences the more contrast agent that is destroyed by the second transmission regions 54 and the less contrast agent that is destroyed by the first transmission regions 52. Brightness may be the particular ultrasound response being detected and compared. If so, to increase the likelihood of a very strong brightness difference between the first and second target zones 64, 68 while imaging after the flash, the second transmission regions 54 may be capable of destroying much or all of the contrast agent in the second target zones 68, and the first transmission regions 52 may destroy little or no contrast agent in the first target zones 64.

Employing a flash comprising more than one frame 40 can increase the brightness difference between the first and second target zones 64, 68. Energy from each frame 40 hits the target 58 and destroys some contrast agent in the second target zones 68, thereby destroying more contrast agent than if a single frame 40 were used for the flash. A multiple-frame flash may thus produce darker second target zones 68 relative to the first target zones 64. If the tissue being flashed is heart tissue, the total duration of the flash should be relatively short so that the heart does not move a large amount during the flash.

The ultrasound machine control console or keyboard 26 may comprise a button or switch to allow an operator to, with one press of the button, flash a target 58 with first and second transmission regions 52, 54 for a pre-determined amount of time and then image the target 58 to reveal the first and second target zones 64, 68 for a pre-determined amount of time.

The actual percentage of contrast agent to be destroyed in the second target zones 68 during the flash may vary for different contrast agents and different tissues being imaged, among other variables. So long as the second target zone or zones 68 have a different ultrasonic response than the first target zone or zones 64 during imaging, then the applications of embodiments of the present invention may be effective regardless of the actual concentration of contrast agent in the first and second target zones 64, 68 following the flash.

The first transmission regions 52 may destroy some of the contrast agent in the first target zones 64. So long as the first target zones 64 have a different ultrasonic response than the second target zones 68, it does not matter that some of the contrast agent in the first target zones 64 is destroyed by the flash. Destruction of contrast agent in the first target zones 64 may be minimized by having the first transmission regions 52 comprise zero energy.

Having created zones having different ultrasonic responses, a number of medical measurements may be made. For instance, blood perfusion rate may be measured as follows by employing an aspect of the present invention. Right after the flash, or just seconds after the flash, the second target zones 68 appear substantially darker than the first target zones 64 when imaged, as shown in FIG. 6. The flash destroys more contrast agent in the second target zones 68 than in the first target zones 64, which causes the second target zones 68 to be darker when imaged. As time elapses following the flash, the second target zones 68 increase in brightness as blood with contrast agent flows into the second target zones 68, replenishing the contrast agent in the second target zones 68. Eventually, as seen in FIG. 7, enough blood will have flowed into the second target zones 68 to cause the concentration of contrast agent in the second target zones 68 to become high enough that, when imaged, the second target zones 68 are substantially as bright as or even as bright as the relatively bright first target zones 64. The time for a measurable brightness difference between the second target zones 68 of FIG. 6 and FIG. 7 is about a couple of heartbeats at minimum, which is about a couple of seconds. In some circumstances, a few dozen seconds may be needed to observe a measurable brightness difference between the second target zones 68 of FIG. 6 and FIG. 7.

To measure the perfusion rate, starting from the moment that the ultrasound energy flash is completed, an operator may measure the time that elapses until the relatively dark or second target zones 68 become substantially as bright as the relatively bright or first target zones 64. To quantify the rate at which the second target zones 68 become brighter following the flash, a graph may be displayed. For example, the graph could show, over time, the brightness of the second target zones 68 relative to neighboring first target zones 64. In many cases, an operator may be able to make accurate perfusion rate measurements without waiting until the second target zones 68 become substantially as bright as the first target zones 64. In such cases, the operator measures the rate at which the second target zones 68 increase in brightness, and the operator concludes the measurements when it appears that a stable perfusion rate measurement has been achieved, even though the second target zones 68 may not yet be substantially as bright as the first target zones 64.

An advantage of using the first and second target zones 64, 68 to assess flow rate is that the first and second target zones 64, 68 may be narrow. By comparing brightness of zones that are close to one another, the reference point (e.g., a point in a first target zone 64) is very close to or local to the zone of interest (e.g., a neighboring second target zone). The first and second target zones 64, 68 that are compared to determine relative brightness may be, but need not be, immediately adjacent one another. More than one first target zone 64 can be compared to more than one second target zone 68.

The optimal width of the first and second target zones 64, 68 may vary for different applications because of different contrast agents, different tissues, and other variables. The narrowness of the stripes 82 that can be formed is limited, in part, by the overlapping of adjacent ultrasound beams 44. Also, it may be undesirable to make stripes 82 very narrow for some applications because very narrow stripes 82 allow blood to flow quickly into the second target zones 68, replenishing the second target zones 68 with contrast agent quickly. For example, very narrow stripes 82 may make it difficult to estimate perfusion rate because the dark regions might lighten too quickly. On the other hand, it may not be desirable in some applications to make the stripes 82 very wide because the locality of tissue may be lost when adjacent stripes 82 are very wide.

Figure 8:
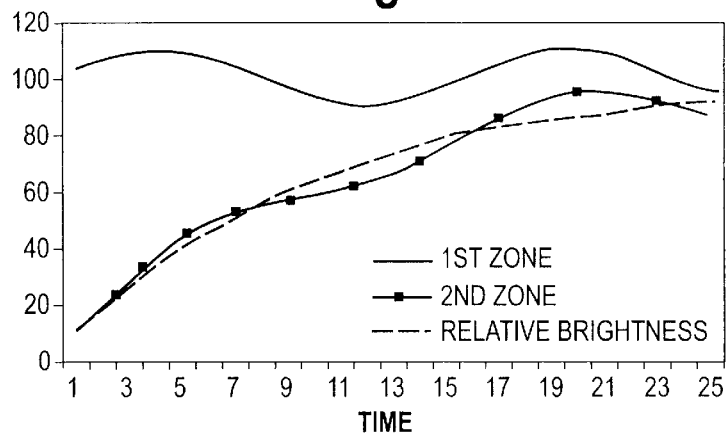
FIG. 8 is a graph of the brightness of the first target zones, the brightness of the second target zones and the relative brightness of the first and second target zones over time following a flash of non-homogeneous energy.

A graph may be made of the absolute brightness of the second target zones 68 over time, from the time a flash of non-homogeneous energy 62 is made to a time when the second target zones 68 become as bright as a pre-determined brightness level. Such a graph might be similar to the line labeled $2^{nd}$ zone in the graph of FIG. 8. The line labeled $2^{nd}$ zone is a line representing the absolute value of brightness of the second target zones 68. FIG. 8 also has a line representing the absolute brightness of the first target zones 64 (labeled $1^{st}$ zone). The units for the vertical axis of the graph may be arbitrary brightness units or ultrasonic response units for the $1^{st}$ zone and $2^{nd}$ zone lines. A third line in FIG. 8 is a line labeled Relative brightness that represents a ratio of the brightness of the second target zones 68 to the brightness of the first target zones 64 at a given time after the flash of non-homogeneous energy 62. The brightness of the first target zones 64 in FIG. 8 over time is not constant following the flash of non-homogeneous energy 62 because the brightness is affected over time by such factors as the heart cycle, breathing movements, and shading. It should be noted that the brightness values and times shown in FIG. 8 are merely examples to show some of the ways in which the first and second target zones 64, 68 may be employed in connection with graphs.

A graph of the absolute value of the brightness of a second target zone 68 may have disadvantages over comparing brightness of a second target zone 68 to the brightness of a nearby first target zone 64. If the target area has unusual blood flow characteristics or unusual tissue depth or shading then the absolute value of the brightness of the second target zone 68 may not accurately correspond to blood flow rate. Rather, a low absolute value of brightness in the second target zone 68 may result from unusually high tissue depth or other variables such as beam 44 energy or focusing. Tissue depth, beam 44 energy, and focusing are just some of the parameters that may affect brightness when imaging with contrast agent. Thus, absolute brightness of the second target zones 68 may not be a reliable indicator of blood perfusion.

Relative brightness of a second target zone 68 compared with a close neighboring first target zone 64 may be a more reliable indicator of perfusion than absolute brightness. This is so because the neighboring first target zone 64 is local tissue and is more likely to be a good indicator of the brightness that should be associated with full perfusion than a distant region or a predetermined absolute brightness value. For instance, distant tissue may have a much faster perfusion rate than the second target zone 68 of interest, the tissues being so distant as to have very different properties. Similarly, the depth of the distant tissue could be different from the second target zone 68, whereas a first target zone 64 adjacent to the second target zone 68 of interest would most likely be of similar depth. Thus, some embodiments of the present invention help overcome the problems of acoustical shades and depth variation artifacts.

Because tissue movement might decrease the accuracy of tissue perfusion measurements, ECG-triggering may be employed to improve accuracy when the heart is the target area 58. ECG-triggering would cause the imaging system to take imaging frames 70 only at particular times in the heart cycle, allowing an operator to compare a particular phase of a heart cycle from one cycle to the next cycle. ECG-triggering may be used to detect differences in brightness for perfusion, and it reduces or excludes artifacts from heart movement.

An advantage of some embodiments of the present invention is that the problem of tissue movement decreasing the accuracy of tissue perfusion measurements can be reduced without ECG-triggering. Neighboring first and second target zones 64, 68 generally move together. Comparison of the brightness of neighboring first and second target zones 64, 68 therefore would not be distorted by tissue movement. In embodiments with stripes 82, neighboring stripes 82 move together and can easily be recognized. This allows for relatively simple tissue tracking on sequential images. The dynamics of local image brightness and, consequently, the local blood perfusion, can be reconstructed more accurately.

Figure 9:
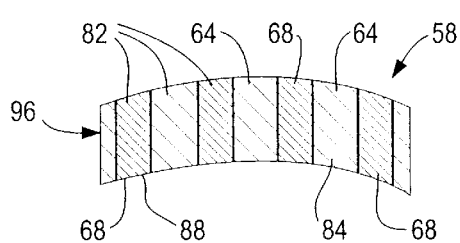
FIG. 9 is a section of the heart that is in a stretched part of the heart cycle and having first and second target zones in accordance with an aspect of the present invention.
Figure 10:
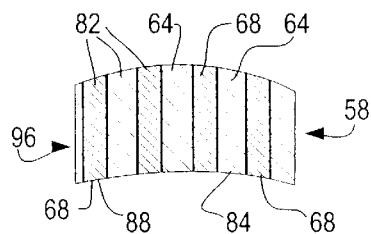
FIG. 10 is the section of the heart that is shown in FIG. 9 depicted during a contracted part of the heart cycle and having first and second target zones in accordance with an aspect of the present invention.

Aspects of the present invention may be used to measure tissue movement. For example, the width of the stripes 82 may be measured so that the level of contractility of the heart during the heart cycle may be measured. Because dead muscle does not contract, heart muscle that is only capable of a little contraction may be detected by employing an aspect of the present invention. In FIG. 9, an image of a section 96 of a myocardium in a relaxed state is shown. FIG. 10, for comparison, shows the same section 96 of a myocardium as FIG. 9 but in a contracted state. As may be seen by comparing FIGS. 9 and 10, the stripes 82 in FIG. 9, which correspond to the relaxed state, are visibly wider than the stripes 82 shown in FIG. 10, which correspond to the contracted state. If the ultrasound machine is set to measure the width of a stripe 82, then the change in the width from the relaxed state to the contracted state may be displayed for an operator of the ultrasound machine, providing the operator with quantitative contractility measurements. The width of a stripe 82 may be measured using ultrasound machine features that are well known for measuring dimensions of ultrasound imaged objects. The width of the stripes 82 may be measured automatically based on tracking of a pattern of first and second target zones 64, 68.

ECG-triggering may be used to help determine when the width measurements should be taken. This way, stripe 82 width measurements may be made during the peak of contraction and the peak of relaxation, so that the width measurements correspond to the points in the heart cycle that are being compared. Other points in the heart cycle may be measured, additionally or alternatively. If desired, the heart cycle may be tracked without ECG-triggering to estimate contractility.

Some embodiments of the present invention may be employed to discriminate between tissue and blood. In medical applications, for example, it may be desirable to image the endocardium (internal surface of the heart ventricle). Such imaging may be desired to estimate ejection fraction, stroke volume, and cardiac output parameters.

However, differences between the myocardium and blood images are often negligible and the tissue/blood border could not be recognized accurately using conventional methods. By exposing heart tissue to a flash to produce the first and second target zones 64, 68 in the tissue, an operator can distinguish blood from the tissue. The blood will become replenished with contrast agent a few seconds following the flash, and will thus be relatively and uniformly light when imaged. The heart tissue, however, will appear to have first and second target zones 64, 68 (e.g., stripes 82) that are relatively light and dark, respectively. The operator will thus see, as shown in FIG. 6, that the heart tissue 78 is striped. A blood/tissue edge detection algorithm may be developed to facilitate distinguishing blood and tissue based on the presence of the first and second target zones 64, 68 that are light and dark, respectively.

Although the heart is the primary body part discussed above, perfusion rates, tissue movement, and blood/tissue discrimination may also be determined for other parts of the body by employing aspects of the present invention. For example, some non-myocardial malignancies can be detected by determining perfusion rates.

The embodiments of the invention described above are not limited to a particular scanning mode. FIGS. 6 and 7 illustrate 2D or B-mode scans. Harmonic power Doppler imaging and other imaging modes may also be employed with aspects of the present invention. Harmonic power Doppler imaging is generally more sensitive to contrast agent concentration than is 2D mode, and may allow imaging with a higher signal-to-noise ratio than is achieved with 2D mode.

Although the first target zones 64 were generally discussed above as being brighter than the second target zones 68 soon after the flash, it is to be understood that video signal processing equipment associated with an ultrasound machine could reverse the brightening effect of the contrast agent. For example, an ultrasound imaging system could display regions having high concentrations of contrast agent as being darker than regions with low concentrations of contrast agent. Thus, an aspect of the present invention is to produce first and second target zones 64, 68 that, when imaged, have different ultrasound responses.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for detecting movement of contrast agent infused heart tissue, the method comprising the steps of:

subjecting the heart tissue to an ultrasound flash capable of producing a plurality of first and second target zones, the first and second target zones being stripes, the first target zones having a higher concentration of contrast agent than the second target zones;

forming an ultrasound image of the heart tissue, wherein the first target zones appear brighter than the second target zones in the ultrasound image; and measuring, over time, a width of at least one of the stripes to detect movement of the heart tissue.

2. The method of claim 1 wherein the step of measuring a width of at least one of the stripes over time is performed to measure an amount of heart relaxation or contraction.

3. The method of claim 1, the measuring step further comprising:

measuring a first width of said at least one of the stripes when the heart is in a relaxed state;

measuring a second width of said at least one of the stripes when the heart is in a contracted state; and calculating a contractility of the heart based upon the first and second widths.

4. The method of claim 1, the measuring step further comprising:

measuring a first width of said at least one of the stripes when the heart is in a relaxed state;

measuring a second width of said at least one of the stripes when the heart is in a contracted state; and calculating a change in width between said first and second widths, said change in width representing a contractility of the heart tissue represented by said at least one of the stripes.

5. A method for producing an ultrasound image of a contrast agent infused target, the method comprising the steps of:

subjecting the target to an ultrasound flash capable of producing a plurality of first and second target zones, the first and second target zones being stripes, the first target zones having a higher concentration of contrast agent than the second target zones;

forming an ultrasound image of the target, wherein the first target zones appear brighter than the second target zones in the ultrasound image; and comparing, over time, a brightness of at least one of the second target zones with a brightness of at least one of the first target zones.

6. A method for producing an ultrasound image of a contrast agent infused target, the method comprising the steps of:

subjecting the target to an ultrasound flash capable of producing a plurality of first and second target zones, the first and second target zones being stripes, the first target zones having a higher concentration of contrast agent than the second target zones;

forming an ultrasound image of the target, wherein the first target zones appear substantially brighter than the second target zones in the ultrasound image;

comparing, over time, a brightness of at least one of the second target zones with a brightness of at least one neighboring first target zone; and measuring an amount of time that elapses from the step of subjecting the target to an ultrasound flash to a time when a ratio between the brightness of the at least one of the second target zones and the brightness of the at least one neighboring first target zone reaches a predetermined value.

7. The method of claim 6 wherein the target comprises heart tissue.

8. The method of claim 6 further comprising measuring a width of at least one of the stripes over time to detect movement of heart tissue.

9. An ultrasound imaging system for calculating blood perfusion in tissue, the system including:

a keyboard for selecting first and second energies used to radiate contrast agent infused tissue for a first predetermined amount of time and for selecting a third energy used to radiate the tissue for a second predetermined amount of time, said first and third energies destroying a relatively small amount of contrast agent and said second energy destroying a relatively large amount of contrast agent;

a front-end controller (FEC) controlling a transducer to radiate, within said first period of time, a plurality of first beam positions forming first transmission regions at said first energy and a plurality of second beam positions forming second transmission regions at said second energy, said FEC radiating the tissue with said third energy for said second predetermined amount of time; and a display for displaying the tissue while the FEC is radiating the tissue with the third energy, said keyboard selecting first and second points within the first and second transmission regions, respectively, said first and second points being used to calculate brightness values for each of said first and second transmission regions, said brightness values representing a perfusion rate of the tissue.

10. The ultrasound system of claim 9, said keyboard setting said first energy to be zero energy.

11. The ultrasound system of claim 9, said FEC forming the first and second transmission regions with an unequal number of beam positions.

12. The ultrasound system of claim 9, said FEC forming each of the first and second transmission regions with 2 to 10 beams.

13. The ultrasound system of claim 9, said FEC forming each of the first and second transmission regions 4 to 6 beams.

14. The ultrasound system of claim 9, said FEC shaping the first transmission region to create a stripe-shaped first target zone and shaping the second transmission region to create a stripe-shaped second target zone.

15. A method for determining a perfusion rate of contrast agent infused tissue, the method comprising:

subjecting contrast agent infused tissue to an ultrasound flash capable of producing a plurality of first and second target zones, said ultrasound flash destroying a first percentage of contrast agent in said first target zones and a second percentage of contrast agent in said second target zones, said second percentage being greater than said first percentage;

acquiring consecutive image frames comprising said first and second target zones, at least one second target zone being substantially brighter than at least one first target zone;

measuring a brightness of said at least one first target zone for each image frame;

measuring a brightness of said at least one second target zone for said each image frame;

comparing, over time, a brightness of said at least one second target zone with a brightness of at least one first target zone to determine a rate of perfusion of said at least one second target zone; and determining a perfusion rate for the tissue based on a ratio of said brightnesses for said each image frame.

16. The method of claim 15, further comprising measuring an amount of elapsed time from the step of subjecting the tissue to said ultrasound flash to a time when said second target zones have substantially the same brightness as said first target zones.

17. The method of claim 15, wherein said first percentage of contrast agent in said first target zones is equal to zero.

18. The method of claim 15, further comprising measuring a rate at which said at least one second target zone increases in brightness.

19. The method of claim 15, said at least one first and second target zones being adjacent.

20. The method of claim 15, said at least one first and second target zones being not adjacent to one another.

21. A method for estimating blood perfusion of tissue, the method comprising:

transmitting first and second ultrasound transmissions within one frame, said first ultrasound transmission being transmitted in at least one first region of tissue and said second ultrasound transmission being transmitted in at least one second region of tissue, said at least one first and second regions of tissue being continuously infused with a contrast agent, said first ultrasound transmission destroying a first percentage of the contrast agent in said at least one first region, said second ultrasound transmission destroying a second percentage of the contrast agent in said at least one second region, said first percentage being greater than said second percentage;

acquiring consecutive image frames comprising said first and second regions of tissue, said first and second regions displaying different ultrasonic responses;

measuring said ultrasound response of said first regions of tissue for each, image frame;

measuring said ultrasound response of said second regions of tissue for said each image frame;

measuring an amount of time that elapses from the transmitting step to a time when an ultrasound response of said second regions is substantially the same as an ultrasound response of said first regions; and determining a perfusion rate for the tissue based on a ratio of said ultrasound responses for said each image frame.

22. The method of claim 21 and comprising the step of:

comparing, over time, the ultrasound response of at least one of the first regions of tissue with the ultrasound response of at least one of the second regions of tissue.

23. The method of claim 21, wherein a number of said first ultrasound transmissions being different from said second ultrasound transmissions is said one frame.

24. A method for identifying an interface between tissue and blood within a contrast agent infused target, the method comprising the steps of:

subjecting a target comprising tissue and blood to an ultrasound flash capable of forming a pattern of acoustic markers, said pattern comprising a plurality of first and second target zones with substantially different brightness levels, said ultrasound flash destroying a first percentage of contrast agent in said first target zones and a second percentage of contrast agent in said second target zones, the first and second percentages being substantially different to produce said first and second target zones;

forming an ultrasound image of the target; and identifying an interface between the tissue and blood based on said pattern of acoustic markers, said pattern of acoustic markers being absent from target zones being produced in areas of the target comprising blood, said pattern of acoustic markers being present in target zones being produced in areas of the target comprising tissue.

25. The method of claim 24, the identifying step further comprising:

calculating, for each target zone, an amount of time required for said each target zone to become substantially the same brightness;

identifying said first and second target zones being produced in the areas of the target comprising blood, said first and second target zones produced in the areas of the target comprising blood being adjacent and having relatively low said amounts of time; and identifying an interfacing target zone, said interfacing target zone having a relatively high said amount of time and being adjacent to a single target zone produced in the areas of the target comprising blood.

26. An ultrasound imaging system for detecting motion in tissue, the system including:

a keyboard for selecting first and second energies used to radiate contrast agent infused tissue for a first predetermined amount of time and for selecting a third energy used to radiate the tissue for a second predetermined amount of time, said first and third energies destroying a relatively small amount of contrast agent and said second energy destroying a relatively large amount of contrast agent;

a front-end controller (FEC) controlling a transducer to radiate, within said first period of time, a plurality of first beam positions forming first transmission regions at said first energy and a plurality of beam positions forming second transmission regions at said second energy, said FEC radiating said first and second transmission regions with said third energy for said second predetermined amount of time; and a display for displaying said first and second transmission regions while the FEC is radiating said first and second transmission regions with the third energy, said keyboard measuring a width of at least one second transmission region over time to detect movement of the tissue.

27. The method of claim 26, further comprising said FEC controlling said transducer to radiate the tissue repeatedly with a sequence comprising said first and second periods of time.

28. The method of claim 26, further comprising:
   said FEC controlling said transducer to radiate heart tissue repeatedly with a sequence comprising said first and second periods of time; and
   said keyboard measuring a width of at least one second transmission region when the heart is at a peak of contraction and when the heart is at a peak of relaxation.

* * * * *